United States Patent [19]
Beck et al.

[11] Patent Number: 5,793,035
[45] Date of Patent: *Aug. 11, 1998

[54] APPARATUS AND METHOD FOR SPRAYING HERBICIDE ON WEEDS IN A COTTON FIELD

[75] Inventors: James L. Beck, Los Gatos; Malcolm L. Kinter, Sunnyvale, both of Calif.

[73] Assignee: Patchen, Inc., Los Gatos, Calif.

[*] Notice: The term of this patent shall not extend beyond the expiration date of Pat. No. 5,585,626.

[21] Appl. No.: 626,857

[22] Filed: Apr. 3, 1996

Related U.S. Application Data

[63] Continuation-in-part of Ser. No. 276,002, Jul. 15, 1994, Pat. No. 5,585,626, which is a continuation-in-part of Ser. No. 149,867, Nov. 10, 1993, Pat. No. 5,389,781, which is a continuation of Ser. No. 920,942, Jul. 28, 1992, Pat. No. 5,296,702.

[51] Int. Cl.$^6$ .................................................. H01J 40/14
[52] U.S. Cl. .................... 250/222.1; 250/226; 356/4.1; 47/1.7
[58] Field of Search ...................... 250/222.1, 226; 356/4.1, 407, 416, 425; 209/580, 581, 582; 47/1.7

[56] References Cited

U.S. PATENT DOCUMENTS

| | | |
|---|---|---|
| 2,514,405 | 7/1950 | Marihart . |
| 2,682,132 | 6/1954 | Marihart . |

(List continued on next page.)

FOREIGN PATENT DOCUMENTS

| | | | |
|---|---|---|---|
| 231270 | 11/1984 | Germany . | |
| 39 00 221 | 7/1989 | Germany . | |
| 229625 | 6/1989 | Netherlands . | |
| 203340 | 12/1967 | U.S.S.R. . | |
| 471074 | 6/1973 | U.S.S.R. . | |
| 382367 | 8/1973 | U.S.S.R. . | |
| 547183 | 4/1977 | U.S.S.R. . | |
| 968631 | 4/1981 | U.S.S.R. | G01J 3/46 |
| 1377606 A1 | 2/1988 | U.S.S.R. | G01J 3/50 |
| 590598 | 7/1947 | United Kingdom . | |
| 2200446 | 8/1988 | United Kingdom | G01J 3/50 |
| WO 84/00211 | 1/1984 | WIPO | G01J 3/46 |

OTHER PUBLICATIONS

W. L. Felton et al., "A Microprocessor Controlled Technology To Selectively Spot Spray Weeds," Dec., 1991.

B. B. Nitsch et al., "Visible And Near Infrared Plant, Soil And Crop Residue Reflectivity For Weed Sensor Design," Paper No. 913006, Jun. 23–26, 1991.

Geoffrey J. Shropshire et al., "Fourier and Hadamard Transforms For Detecting Weeds in Video Images," Paper No. 89–7522, Dec. 12–15, 1989.

Geoffrey J. Shropshire et al., "Optical Reflectance Sensor for Detecting Plants," SPIE vol. 1379, 1990.

UDT Sensors, Inc., Optoelectronic Components Catalog, Apr. 1992, p. 33.

*Primary Examiner*—Que Le
*Assistant Examiner*—Kevin Pyo
*Attorney, Agent, or Firm*—Skjerven, Morrill, MacPherson, Franklin and Friel L.L.P.; T. Lester Wallace

[57] ABSTRACT

Weeds growing around the bases of the stalks of cotton plants growing in a row in a cotton field are sprayed with herbicide without spraying the cotton stalks or wasting herbicide on bare ground. The cotton plants are adequately mature that their stalks exhibit a significantly different spectral reflectance characteristic than the weeds typically growing amid the cotton. The cotton plants are adequately tall that the majority of the leaves of the cotton plants are disposed outside the area which can be sprayed using an electronically-controlled valve and nozzle. Light is transmitted toward an object (a cotton stalk, a weed, or soil) in the row and the reflected light is analyzed. If the object has a spectral characteristic of a growing weed, then the valve is activated and the object is sprayed with herbicide. If the object does not have the spectral characteristic of a growing weed (such as the spectral characteristic of a woody cotton stalk or of soil), then the valve is not activated and the object is not sprayed with herbicide.

14 Claims, 11 Drawing Sheets

U.S. PATENT DOCUMENTS

| | | |
|---|---|---|
| 2,894,178 | 7/1959 | Chesebrough . |
| 3,168,238 | 2/1965 | Carrigan . |
| 3,373,870 | 3/1968 | Black . |
| 3,488,511 | 1/1970 | Mori et al. . |
| 3,512,587 | 5/1970 | Shader . |
| 3,590,925 | 7/1971 | Koelsch et al. . |
| 3,609,913 | 10/1971 | Rose . |
| 3,652,844 | 3/1972 | Scott, Jr. . |
| 3,701,218 | 10/1972 | Priest . |
| 3,821,550 | 6/1974 | Priest . |
| 3,910,701 | 10/1975 | Henderson et al. .......... 356/39 |
| 4,015,366 | 4/1977 | Hall, III . |
| 4,029,391 | 6/1977 | French ..................... 350/96 C |
| 4,092,800 | 6/1978 | Wayland, Jr. et al. . |
| 4,179,216 | 12/1979 | Theurer et al. . |
| 4,206,569 | 6/1980 | Randolph ..................... 47/1.7 |
| 4,369,886 | 1/1983 | Lane et al. . |
| 4,482,960 | 11/1984 | Pryor . |
| 4,527,897 | 7/1985 | Okabe . |
| 4,550,526 | 11/1985 | Smucker . |
| 4,558,786 | 12/1985 | Lane . |
| 4,618,257 | 10/1986 | Bayne et al. . |
| 4,699,273 | 10/1987 | Suggi-Liverani et al. . |
| 4,709,265 | 11/1987 | Silverman et al. . |
| 4,768,713 | 9/1988 | Roper . |
| 4,989,783 | 2/1991 | Douglas . |
| 4,991,341 | 2/1991 | Douglas . |
| 5,006,719 | 4/1991 | Blaser ..................... 250/560 |
| 5,015,868 | 5/1991 | Park . |
| 5,021,645 | 6/1991 | Satula et al. ............ 250/223 R |
| 5,068,540 | 11/1991 | Tsuji ..................... 250/559.38 |
| 5,072,128 | 12/1991 | Hayano et al. . |
| 5,109,161 | 4/1992 | Horiuchi et al. ......... 250/559.38 |
| 5,144,767 | 9/1992 | McCloy et al. . |
| 5,222,324 | 6/1993 | O'Neall et al. . |
| 5,233,177 | 8/1993 | Kobayashi et al. ......... 250/208.1 |
| 5,237,386 | 8/1993 | Harley ..................... 356/338 |
| 5,278,423 | 1/1994 | Wangler et al. . |
| 5,296,702 | 3/1994 | Beck et al. . |
| 5,319,196 | 6/1994 | Cleven ..................... 250/231.13 |
| 5,347,122 | 9/1994 | Ansorge et al. ......... 250/227.11 |
| 5,386,285 | 1/1995 | Asayama ..................... 356/4.01 |
| 5,389,781 | 2/1995 | Beck et al. ..................... 250/226 |
| 5,585,626 | 12/1996 | Beck et al. ..................... 250/222.1 |

Separate (discrete) outputs of detector

Continuous (proportional) output of detector

Top-Down View

Side View

APPARATUS AND METHOD FOR SPRAYING HERBICIDE ON WEEDS IN A COTTON FIELD

CROSS REFERENCE TO RELATED APPLICATIONS

This application is a continuation-in-part of application Ser. No. 08/276,002, filed Jul. 15, 1994 (now U.S. Pat. No. 5,585,626), which in turn is a continuation-in-part of application Ser. No. 08/149,867 (now U.S. Pat. No. 5,389,781), filed Nov. 10, 1993, which in turn is a continuation of application Ser. No. 07/920,942, filed Jul. 28, 1992 (now U.S. Pat. No. 5,296,702).

FIELD OF THE INVENTION

The present invention relates to the optical detection of objects. More particularly, the present invention relates to applying herbicide onto weeds in a field of cotton.

BACKGROUND INFORMATION

U.S. Pat. No. 5,296,702 discloses structures and methods for differentiating living plants from soil. Living plants have a spectral reflectance characteristic in regions of the electromagnetic spectrum which differs from the spectral reflectance characteristic of soil. By transmitting light of a first wavelength and light of a second wavelength onto an object and detecting the relative magnitudes of the reflected light of the two wavelengths, it can be determined whether the object has the spectral reflectance characteristic of a living plant or the spectral characteristic of soil. To conserve herbicide in agricultural spraying operations, living plants so differentiated from soil are sprayed with herbicide and the bare ground (which does not have the spectral characteristic of a living plant) is not sprayed. Cotton plants are, however, living plants. A device is therefore desired which will spray herbicide onto weeds growing between and around the cotton plants without killing the cotton plants themselves.

SUMMARY

Weeds growing around the bases of the stalks of cotton plants are sprayed with herbicide without spraying the cotton stalks or wasting herbicide on bare ground. The cotton plants are adequately mature that their stalks exhibit a significantly different spectral reflectance characteristic than the weeds typically growing amid the cotton. The cotton plants are adequately tall that the majority of the leaves of the cotton plants are disposed outside the area which can be sprayed using an electronically-controlled valve and nozzle. Light is transmitted toward an object and the reflected light is analyzed. If the object has a spectral characteristic of a growing weed, then the valve is activated and the object is sprayed with herbicide. If the object does not have the spectral characteristic of a growing weed (such as the spectral characteristic of a woody cotton stalk or of soil), then the valve is not activated and the object is not sprayed with herbicide.

This summary does not purport to define the invention. The invention is defined by the claims.

DETAILED DESCRIPTION OF THE PREFERRED EMBODIMENTS

Figure 1:
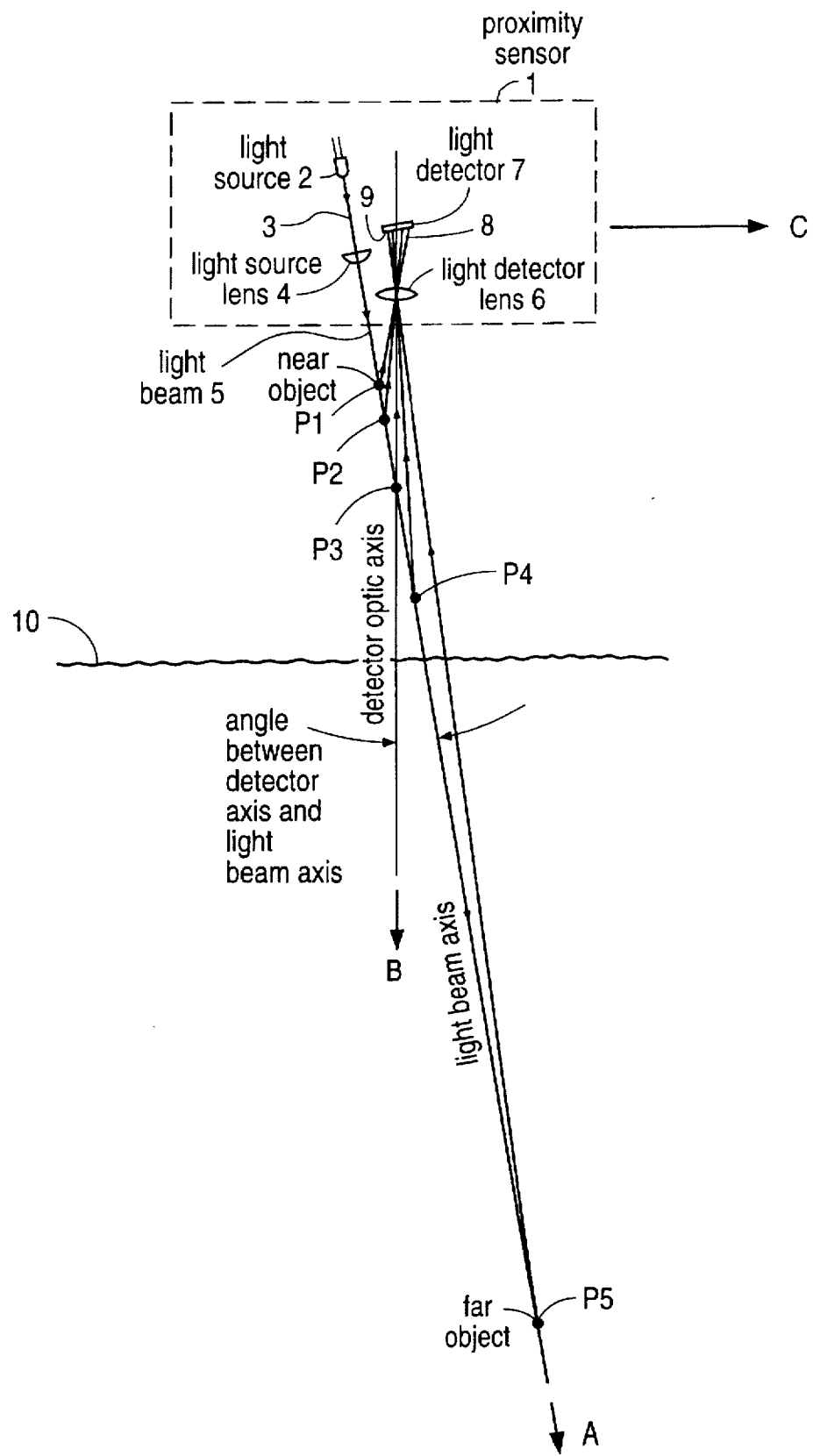
FIG. 1 illustrates a proximity determining sensor.

FIG. 1 illustrates a proximity determining sensor 1. Proximity determining sensor 1 comprises a source of light 2 which generates light 3, a light beam forming lens 4 which forms light 3 into a light beam 5, a detector lens 6, and a light detector 7. Light beam 5 is aligned in direction A. Detector lens 6 has an optic axis in direction B. If, for example, light from light beam 5 reflects off an object located at point P1, then reflected light from the light beam will be incident on light detector 7 at a near image position 8. If, on the other hand, light from light beam 5 reflects off an object located at a distant point P5, then reflected light from the light beam 5 will be incident on the light detector 7 at a far image position 9. Reflections of light from light beam 5 at several intermediate positions P2–P4 are also illustrated in FIG. 1. Sensor 1 may, for example, be moved in direction C with respect to the surface 10 of the ground in an open field so that light beam 5 is scanned over surface 10.

In one specific embodiment of FIG. 1, the light of light beam 5 is generated by a plurality of light emitting diodes arranged in a row. Only one of the light emitting diodes is illustrated in FIG. 1 because the row of light emitting diodes extends in the direction perpendicular to the plane illustrated. Light beam forming lens 4 is a cylindrical lens which has a longitudinal axis which extends in the direction of the row of light emitting diodes. Light beam 5 therefore is a relatively thin sheet of light having a first dimension which extends in the direction perpendicular to the illustrated plane and having a second dimension, the direction of travel of the light, which extends in direction A.

In some embodiments, light detector 7 is a silicon PIN photodiode Model No. SL3-2, manufactured by UDT Sensors, Inc., Hawthorne, Calif. Other suitable photodetectors may be used. In some embodiments, a charge coupled device (CCD) may be used. In some embodiments, lens 4 is a cylindrical lens approximately 3 inches long and approximately 1 inch wide having a focal distance of approximately 0.8 inches, available from United States Precision Lens. In some embodiments, detector lens 6 is a plano-convex lens approximately 1.5 inches in diameter having a focal distance of approximately 1.5 inches available from United States Precision Lens. The angle between directions A and B is about 7.1 degrees, the lateral distance between light source 2 and light detector 7 is about 2.8 inches, and the distance between light detector lens 6 and light detector 7 is about 2.5 inches.

Figure 2A:
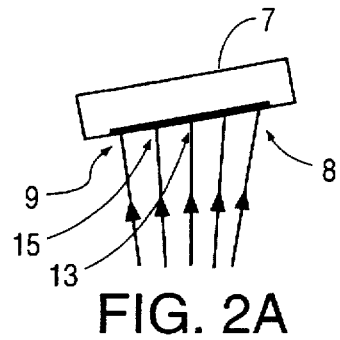
FIGS. 2A–2C are cross-sectional views of a light detector of the sensor of FIG. 1.

FIG. 2A is a cross-sectional view of the light detector 7 of FIG. 1 showing near image position 8 and far image position 9 in greater detail. The image plane of the detector surface of light detector 7 is slanted with respect to the optic axis of light detector lens 6 in order to maintain focus of the light arriving from the various object positions P1–P5.

Figure 3A:
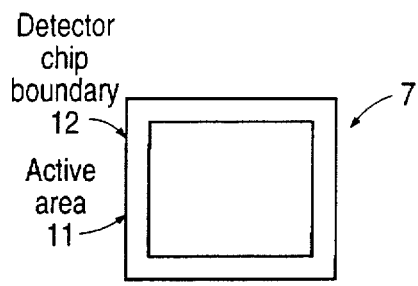
FIGS. 3A–3E are plan views of a light detector illustrating an operation of the sensor of FIG. 1.

FIG. 3A is a plan view of the detector surface of the light detector 7 of FIG. 1 looking up into light detector 7 in the direction opposite to direction B. Light detector 7 has an active area 11 and a chip boundary 12.

Figure 4B:
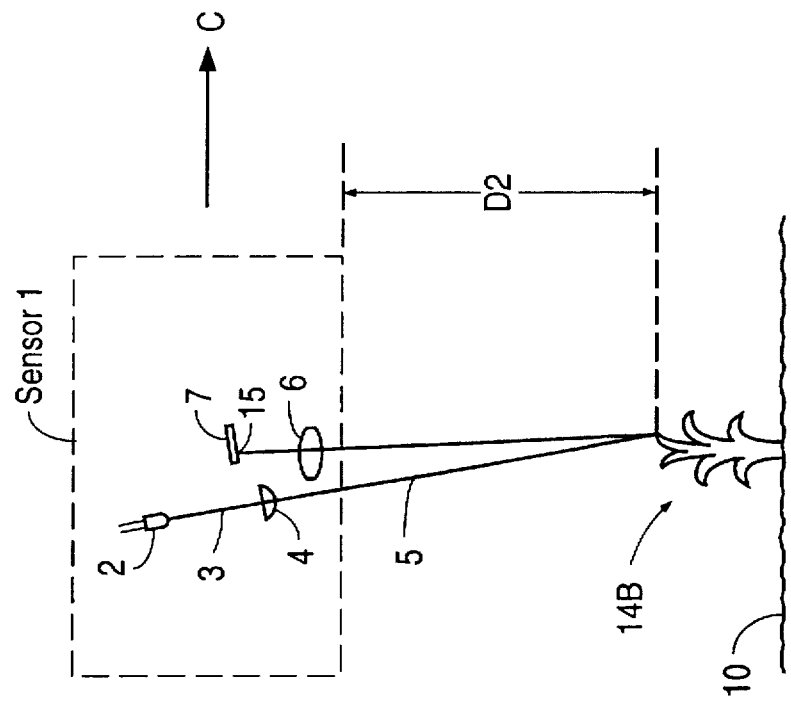
FIGS. 4A and 4B are views of an operation of the sensor of FIG. 1.
Figure 4A:
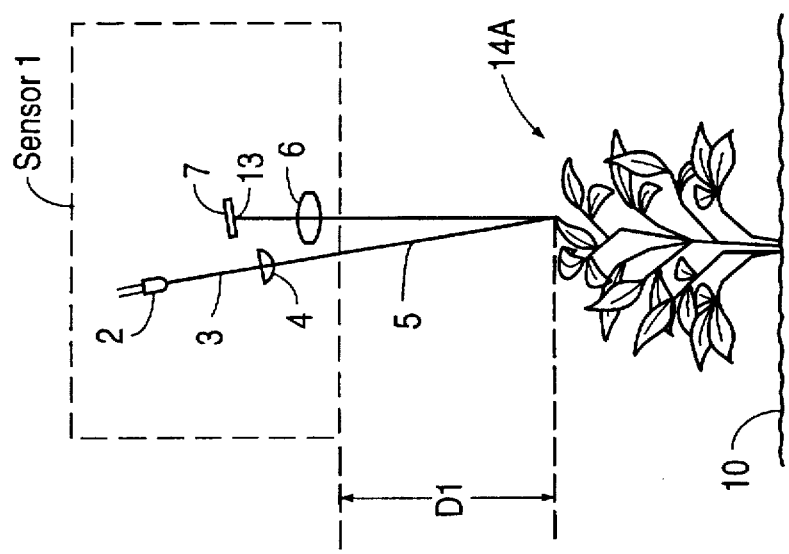

FIGS. 4A and 4B are diagrams illustrating sensor 1 at two points in time when sensor 1 is moved in direction C with respect to the surface 10 of a field. As illustrated in FIG. 4A, when at a first point in time light from light beam 5 is reflected off a surface of a relatively tall living plant 14A at a distance D1 from sensor 1, an image of the reflected light is formed on light detector 7 at image position 13. As illustrated in FIG. 4B, when at a second point in time sensor 1 has moved farther in the direction C with respect to the surface 10 of the field, light from light beam 5 is reflected off a surface of a relatively short living plant 14B at a distance D2 from sensor 1. An image of the reflected light is formed on light detector 7 at image position 15. Accordingly, the position of the image of the reflected light on light sensor 7 is indicative of the distance of the reflecting object. The angle between the detector axis and the light beam axis is set so that light reflected from light beam 5 strikes the center of the light detector 7 for an object located at a predetermined distance from sensor 1. This allows for a large variation in sensor-to-object distance.

Figure 2B:
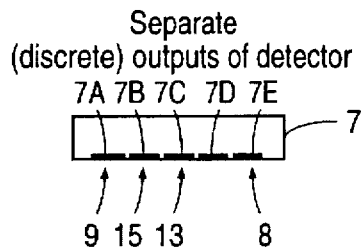

FIG. 2B is a cross-sectional view of one embodiment of light detector 7. Light detector 7 actually comprises a plurality of smaller detectors 7A–7E. If the image created by the light reflecting off the relatively tall living plant 14A is formed at image position 13 on detector 7C, then a corresponding signal will be generated on an output terminal of detector 7C. If, on the other hand, the image created by the light reflected off the relatively short living plant 14B is formed at image position 15 on detector 7B, then a corresponding signal will be generated on an output terminal of detector 7B. The distance from the sensor 1 to the object 14A, 14B is determined by identifying from which particular detector of detectors 7A–7E the signal emanates.

Figure 2C:
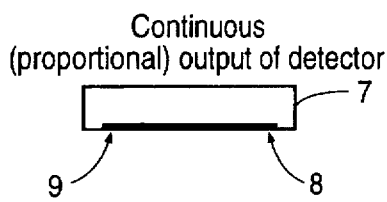

FIG. 2C is a cross-section view of another embodiment of light detector 7. Light detector 7 comprises a single detector, the near image position 8 being at one end of the detector active area, the far image position 9 being at an opposite end of the detector active area. Such a light detector has an additional anode terminal, the relative magnitude of the signals present on the two anode terminals being indicative of the relative position of the image between two ends of the active area of the detector. The distance from the sensor 1 to the object 14A, 14B is therefore determined by comparing the relative magnitudes of the two anode signals due to the reflected image.

Figure 5:
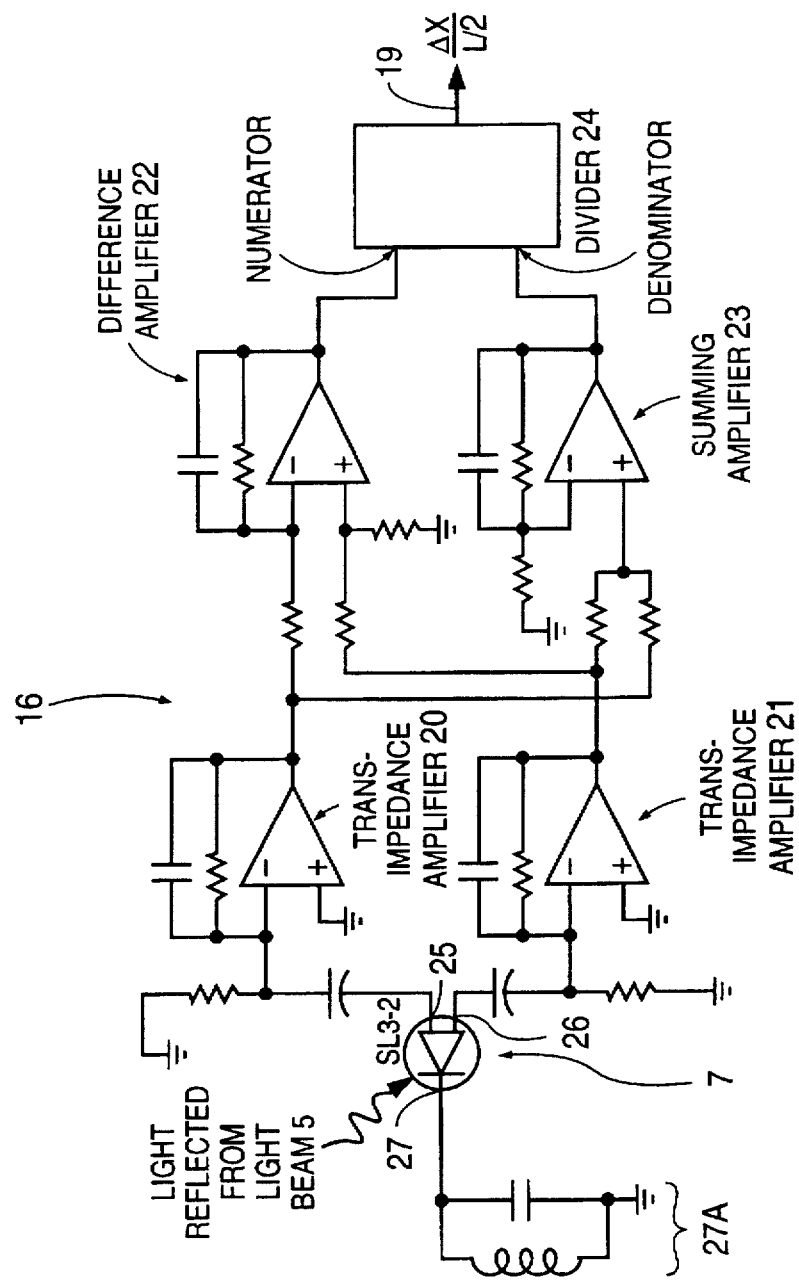
FIG. 5 is circuit diagram showing one embodiment of a circuit of the sensor of FIG. 1 which generates a signal indicative of a distance to an object.

FIG. 5 is a circuit diagram showing one embodiment of a circuit 16 of sensor 1 which generates a signal on terminal 19, the voltage of the signal being indicative of a relative distance between a reflecting object 14A, 14B and sensor 1. The specific embodiment illustrated in FIG. 5 comprises a first trans-impedance amplifier 20, a second trans-impedance amplifier 21, a difference amplifier 22, a summing amplifier 23, and a divider 24. Anode terminals 25 and 26 of light detector 7 may, for example, correspond with near image position 8 and far image position 9 of a single detector light detector 7, respectively. Light detector 7 has a cathode 27 coupled to an LC circuit 27A. Light detector 7 can be reverse biased or can be operated in the photovoltaic mode as shown. The LC circuit 27A is provided to discriminate sunlight as explained below. The magnitude of an analog voltage generated on the output terminal 19 of divider 24 is proportional to a distance to a reflecting object. This distance information in the form of an analog voltage is converted to a digital representation before being processed in a microcontroller. In some embodiments, output terminal 19 is coupled to an analog-to-digital converter input pin of a microcontroller (not shown).

Not only is light reflected from light beam 5 incident on light detector 7, but light from other sources may also be incident on light detector 7. When, for example, the sensor 1 is operated in broad daylight in an open field, sunlight is reflected off objects and back up into sensor 1. Moreover, because the sunlight is not focussed into a beam, reflected sunlight is incident on the entire detecting surface of light detector 7. Sensor 1 distinguishes reflected sunlight from reflected light from beam 5 using techniques disclosed in U.S. patent application Ser. No. 07/920,942 (now U.S. Pat. No. 5,296,702), the contents of which are incorporated herein by reference. In one embodiment, light 3 from light source 2 is modulated with a modulation signal having a frequency. The LC filter circuit 27A is tuned to the modulation frequency and therefore passes energy at the frequency of the modulation signal and attenuates energy at other frequencies. Accordingly, the component of the signal output by light detector 7 which is due to reflections of light beam 5 is distinguished from components of the signal output by light detector 7 which are due to the more slowly varying ambient sunlight.

In some embodiments, a phase difference between the signal output on output terminal 19 of the circuit of FIG. 5 and a modulation signal used to modulate the light 3 emitted from light source 2 is used by a microcontroller to determine whether an illuminated object is a plant. The phase of the signal oscillating in LC circuit 27A is determined by the phase of the radiation received. If more radiation modulated with a first phase is received, the signal oscillating in LC circuit 27A will have a phase relatively closer to the first phase whereas if more radiation modulated with a second phase is received, the signal oscillating in the LC circuit 27A will have a phase relatively closer to the second phase. Both distance information and spectral characteristic information are therefore provided by the same circuit of FIG. 5. In other embodiments, a separate circuit such as is set forth in U.S. patent application Ser. No. 07/920,942 (now U.S. Pat. No. 5,296,702) is provided to determine whether the illuminated object is a plant so that distance information is provided by the circuit of FIG. 5 and spectral characteristic information is provided by a separate circuit.

In some embodiments, a plurality of units such as sensor 1 is aligned in a row such that the row of units senses objects disposed in a narrow illuminated strip and such that each individual unit senses a corresponding section of the strip. The light of light beam 5, however, may diverge somewhat in the direction perpendicular to the plane illustrated in FIG. 1 so that a band of an object illuminated by beam 5 at near position P1 has a relatively short length whereas that same band illuminated by beam 5 at far location P5 has a relatively long length. In order to control the field of view of the unit over a range of object distances and prevent overlap of the fields of view of adjacent units, an image mask 28 is disposed between detector lens 6 and light detector 7.

Figure 3B:
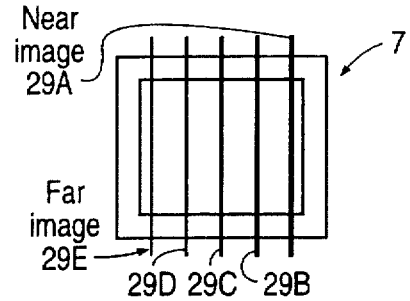
Figure 3C:
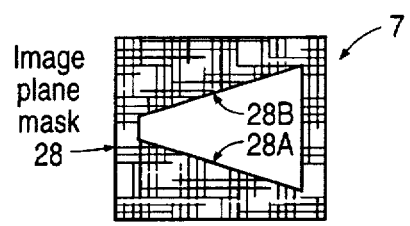
Figure 3D:
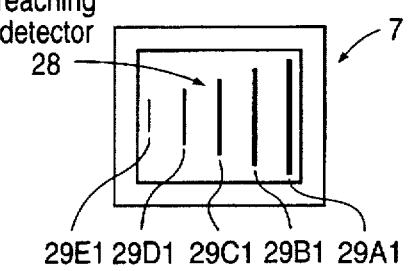
Figure 3E:
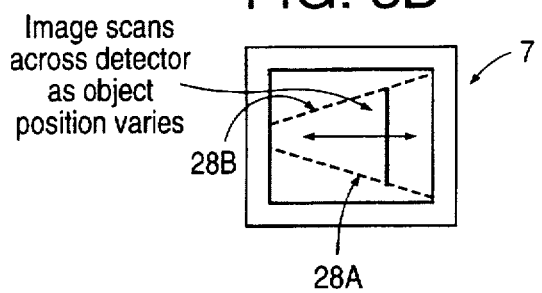

FIG. 3B illustrates five images 29A–29E corresponding with light of beam 5 reflected from positions P1–P5, respectively. FIG. 3C illustrates an image plane mask 28. An opening of image plane mask 28 has a first edge 28A which is non-parallel with respect to a second edge 28B opposite the first edge. FIG. 3D illustrates the images 29A1–29E1 which are incident upon the detector surface of light detector 7 due to the operation of image plane mask 28. Image 29E1 corresponds with the same illuminated object distance on a distant object located at position P5 as does object image 29A1 on a close object located at position P1. FIG. 3E illustrates the image incident on the detecting surface of light detector 7 moving back and forth across the detecting surface as a distance between an object illuminated by light beam 5 is moved toward and away from sensor 1.

In accordance with some embodiments, light of light beam 5 reflected back into sensor 1 is also analyzed to determine a spectral characteristic of an object from which the light reflected. Depending on the spectral reflectance characteristic detected, a determination can be made as to whether the object is a plant. Accordingly, a sensor in accordance with some embodiments develops information indicative of whether an object illuminated by light beam 5 is a plant in addition to information indicative of a distance between the sensor and the object.

Figure 6:
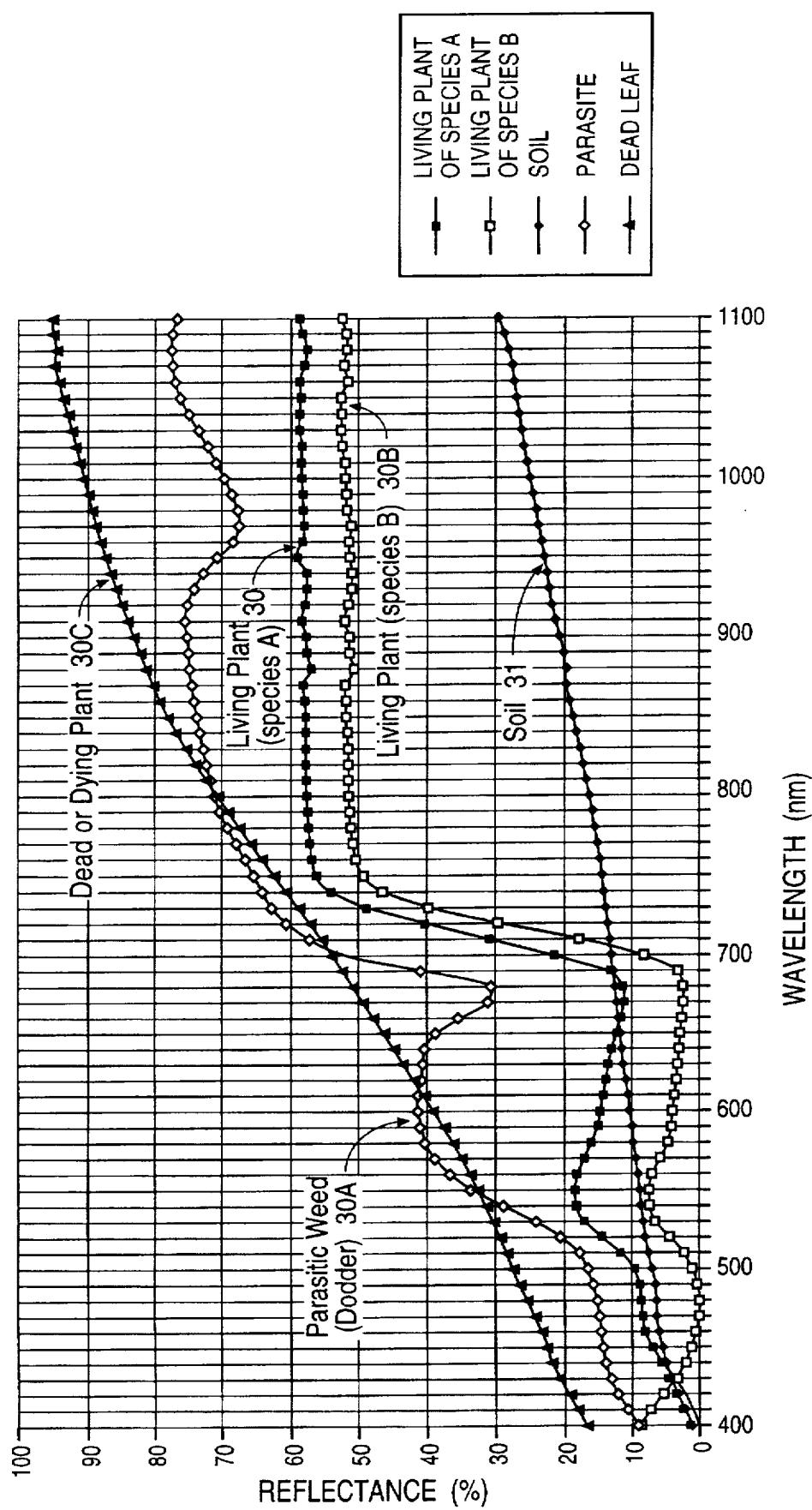
FIG. 6 is a diagram illustrating different spectral reflection characteristics of a living plant, a dead leaf, soil, and a parasitic weed over a wavelength range of 400–1100 nm.

FIG. 6 is a diagram illustrating how certain living plants, a dead or dying plant, soil, and a parasitic weed reflect light having different wavelengths over the wavelength range of 400–1100 nm. Lines 30, 30A, 30B, 30C and 31 of the graph of FIG. 6 indicate spectral characteristics of a living plant of a first species A, a parasitic weed, a living plant of a second species B, a dead or dying plant and soil, respectively. By detecting a relative reflectance of light off an object at two wavelengths (for example, 670 nm and 750 nm) it is possible to distinguish light reflected from living plants from light reflected from soil. By detecting a relative reflectance of light off an object at two wavelengths (for example, 645 nm and 750 nm), it is possible to distinguish light reflected from living chlorophyll bearing plants from light reflected from certain parasitic weeds. By detecting a relative reflectance of light off an object at two or more wavelengths (for example, 430 nm, 575 nm and 750 nm), it is possible to distinguish light reflected from various living chlorophyll bearing plants of certain species from other chlorophyll bearing plants of other species. It is possible to distinguish the difference between rice and water grass in this fashion. A more detailed description of a technique for determining whether an object is a living plant or is soil is set forth in U.S. patent application Ser. No. 07/920,942 (now U.S. Pat. No. 5,296,702).

Therefore, in accordance with some embodiments, light 3 comprises light having a first wavelength and light having a second wavelength. The light having a first wavelength is modulated with a first modulation signal whereas the light of the second wavelength is modulated with a second modulation signal. In a preferred embodiment, the first modulation signal has the same frequency as the second modulation signal but is offset in phase with respect to the second modulation signal. In accordance with the technique disclosed in U.S. patent application Ser. No. 07/920,942 (now U.S. Pat. No. 5,296,702), the relative magnitude of the component of a signal output by light detector 7 due to the light of the first wavelength with respect to the component of the signal output by light detector 7 due to the light of the second wavelength is determined. A relative magnitude corresponding with corresponding points on line 30 is indicative of a reflection off a plant whereas a relative magnitude corresponding with corresponding points on line 31 is indicative of reflection off soil. Although one technique for developing information indicative of whether an object is a plant is set forth here for illustrative purposes, it is to be understood that other techniques which take advantage of the different reflectance characteristics of different objects may be employed in sensor 1.

Large object size to image size reductions (high demagnification) when the object is close to the light detector lens can be difficult to realize. Light rays converging to the image focus are at a large included angle and the depth of field is small. Light detector lens 6 may therefore be a somewhat expensive lens and it may be difficult to adjust lens 6 mechanically in order to achieve a proper focus of the reflected light onto the detecting surface of the light detector 7. To overcome these difficulties, the image is focussed at a convenient lower demagnification with a lower power light detector lens 6 and a non-imaging tapered light pipe is used to effect a spatial compression of the light of the image where distance determination or proximity sensing is not performed by light detector 7. Accordingly, system cost is reduced and mechanical adjustment tolerances are relaxed.

Figure 7A:
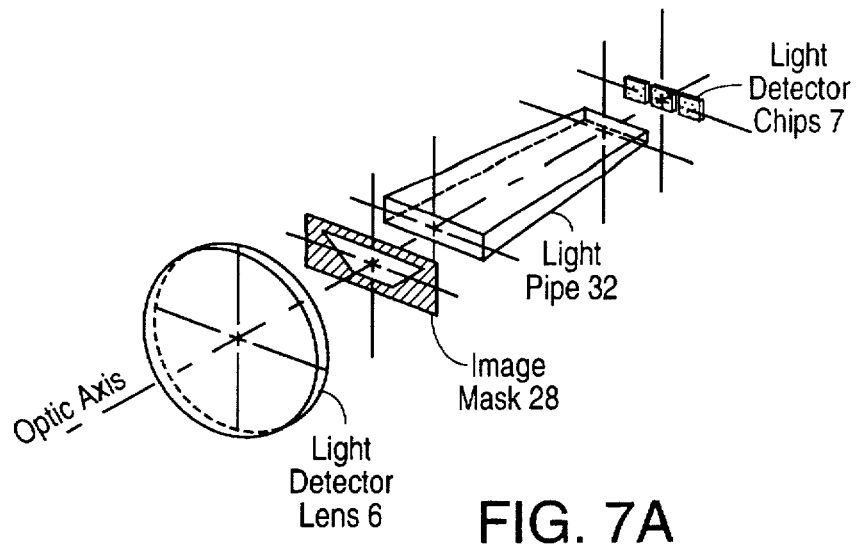
FIGS. 7A–7D are diagrams illustrating a light pipe in accordance with some embodiments.
Figure 7B:
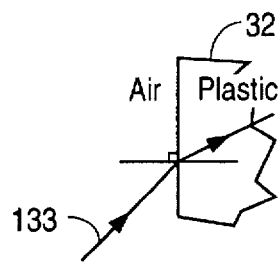
Figure 7C:
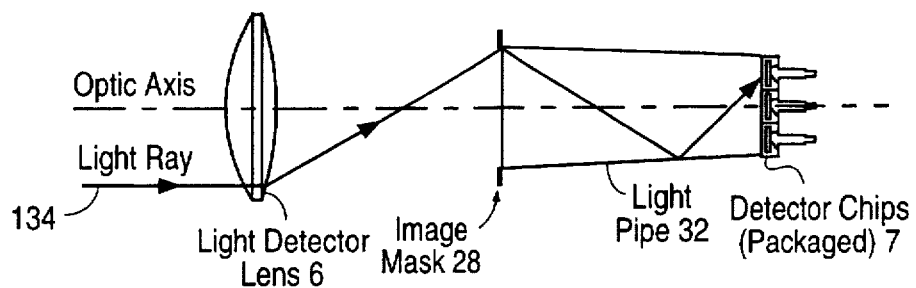
Figure 7D:
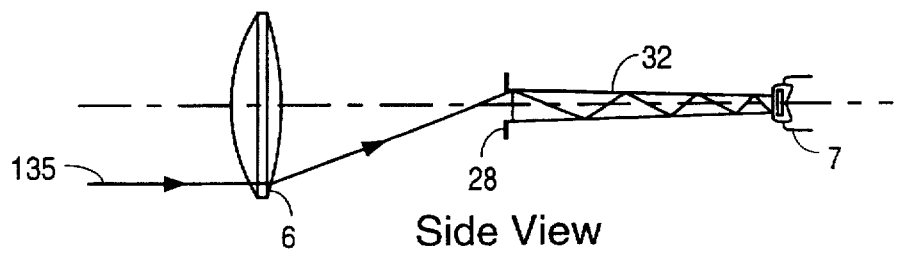

FIG. 7A shows a light pipe 32 disposed between image mask 28 and light detector 7. Light detector 7 comprises a plurality of light detector chips. Due to the inclusion of light pipe 32, light detector lens 6 need not focus on the relatively small detector surface. Rather, a ray of light 133 passes into light pipe 32 as illustrated in FIG. 7B. FIG. 7C is a top-down view illustrating a ray of light 134 passing through light detector lens 6, through the opening in image mask 28, into light pipe 32, and onto light detector 7. FIG. 7D is a side view illustrating a ray of light 135 passing through light detector lens 6, through the opening in image mask 28, through light pipe 32, and to light detector 7. Due to the tapered shape of the light pipe 32, the light reflected off the object reflects down the light pipe and onto the smaller light detector surface.

The methods set forth below do not constitute an exhaustive treatment of all uses of the present distance determining technique but are merely illustrative.

Method #1

Spraying Weeds Growing in the Ground Around Trees

Figure 8A:
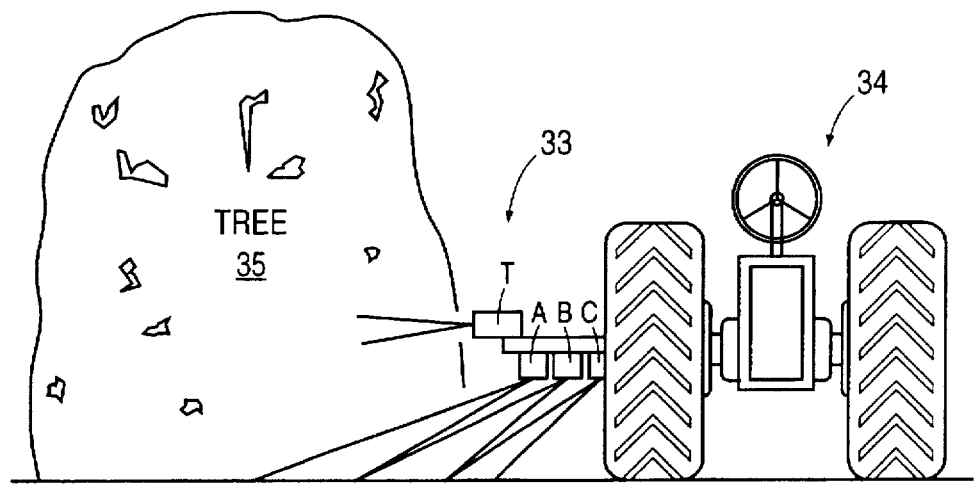
FIGS. 8A and 8B are diagrams illustrating the spraying of herbicide around the base of a tree.
Figure 8B:
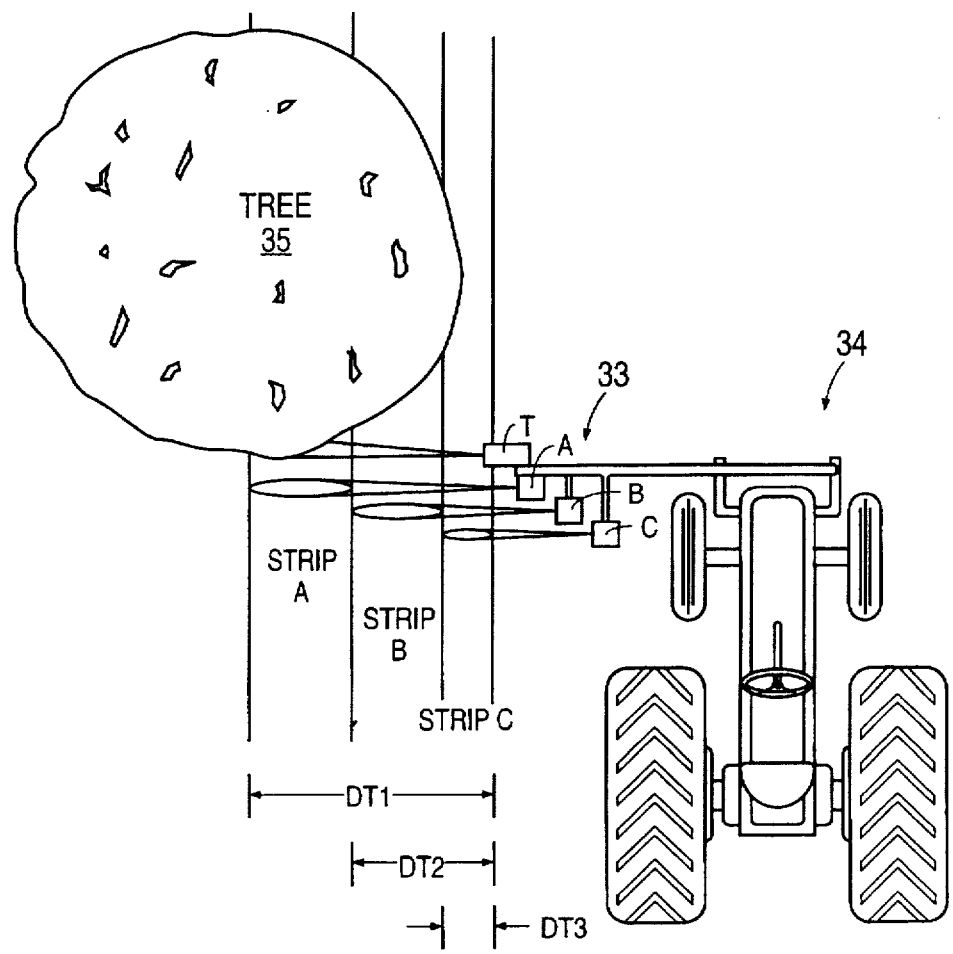

FIGS. 8A and 8B are diagrams illustrating an orchard sprayer 33 for spraying weeds growing in the ground around trees. Orchard sprayer 33 comprises four sensors denoted T, A, B and C in FIGS. 8A and 8B. Each of the sensors comprises a plurality of light emitting diodes which emits a narrow long light beam. The narrow long light beams emitted from sensors A, B and C are directed toward the ground as illustrated in FIG. 8B such that strips of the ground A, B and C are scanned by light beams from sensors A, B and C, respectively, as a means for moving 34 moves the orchard sprayer with respect to the tree 35. The light beam emitted from sensor T is, on the other hand, directed in a substantially horizontal direction so as not to illuminate weeds on the ground but so as to be reflected off tree 35 as illustrated in FIG. 8A.

Each of the three sensors A, B and C is coupled to a corresponding row of electrically-controlled valves, pumps, or injectors (not shown) so that a plant detected by one of the sensors will be sprayed by nozzles controlled by that sensor. In one embodiment, each of the electronically-controlled valves (such as part number AM2106 available from Angar Scientific) has an associated spray nozzle and therefore forms an electronically-controlled spray nozzle.

In order to spray weeds on the ground around tree 35 without spraying the tree itself, a distance to tree 35 is determined by sensor T as the means for moving 34 moves the orchard sprayer past the tree. A short time after sensor T detects an object having a spectral reflectance characteristic indicative of a living plant (which in this case would be tree 35) at a distance between distance DT1 and DT2, the spray nozzles of sensor A are disabled so that tree 35 will not be sprayed. The spray nozzles coupled to sensors B and C, however, remain enabled so that weeds growing in the ground in strips B and C will be sprayed. Sensors B and C only cause objects having a spectral characteristic of a living plant to be sprayed and therefore do not waste herbicide by spraying the bare ground. After the means for moving 34 propels the orchard sprayer farther so that sensor T detects tree 35 at a distance between distance DT2 and DT3, sensors A and B are disabled leaving only sensor C to detect and spray weeds in strip C. Again, sensor C only causes objects having a spectral reflectance of a living plant to be sprayed. When the orchard sprayer has moved to the opposite side of the tree, the spray nozzles for the corresponding strips are enabled in reverse order as sensor T detects the distance to tree 35 getting larger, thereby spraying weeds in the ground around tree 35 and not spraying herbicide onto the tree itself.

In the illustration, sensors T, A, B and C are mounted in a staggered configuration on means for moving 34 in the direction of travel. The sensors A, B and C would therefore be disabled and enabled an appropriate amount of time after the tree is detected by sensor T so that weeds in the corresponding strip will be sprayed right up to the edge of the tree without spraying the tree. The speed of the means for moving 34 is therefore detected and used to determine when to enable and disable the spray nozzles. In order to prevent the spray from interfering with the optics of the plant detecting operation, the weeds are not sprayed when they are detected but rather are sprayed at a later time as explained in U.S. patent application Ser. No. 07/920,942 (now U.S. Pat. No. 5,296,702).

Method #2

Spraying Trees and not Spaces Between Trees

In accordance with another embodiment, an orchard sprayer detects a tree and then controls spray nozzles to spray the tree with a chemical material (such as pesticide and other foliar applied materials) so that the chemical material is not wasted in the spaces between trees. Because a distance sensor is able to determine whether or not the reflected light has a spectral characteristic of a living plant, such an orchard sprayer distinguishes non-plant objects from living trees, thereby overcoming the above described problem of spraying barns and people associated with prior art orchard sprayers. In some embodiments, material flow is switched on and off depending on the total biomass detected in the field of view and the distance to the biomass. Fluid pressure, nozzle configuration, nozzle direction and other parameters of the spraying operation are also automatically adjusted to accommodate the particular size, density and distance to the biomass. This technique is also usable for selectively dispensing herbicide on weeds along roads, highways and railroad tracks.

Method #3

Row Crop Middle Selective Weed Sprayer

Many crops grow in rows where the spacing between rows is fixed by the planting or seeding implement. Such row crops include corn, soybeans, tomatoes and cotton. The space between adjacent rows is referred to as the "middle" and often should be kept free of weeds in order to optimize crop yield and to minimize harvesting problems. Traditionally this middle has been kept free of weeds by mechanical cultivation. This technique has limitations. First, tilling or breaking up the soil requires large equipment and therefore large amounts of energy. Second, so-called "cultivator burn" results from getting too close to the row with the cultivator tines and damaging plant roots. Third, tilling opens the soil to the air thereby allowing moisture to escape and making the soil subject to erosion from wind and rain.

Spraying weeds in the middles with herbicide may therefore be considered a more desirable method of eliminating weeds from the middles. Two principal difficulties with spraying weeds are cost of the herbicide material and the potential of contaminating the environment with excessive chemicals. Both of these problems are addressed by aspects of the present embodiment.

Weeds in middles are generally found in patches ranging from a few inches across to a few feet across. It is generally not practical for a spray vehicle operator to turn the sprayer off and on, each time a patch of weeds is encountered. Therefore a preferred technique is to rely heavily on preemergence herbicide to discourage weed seeds from germinating and then later spraying a continuous blanket of post emergence herbicide in the middles to eliminate any weeds which germinated despite the preemergence herbicide. Selective spraying using the optical detection technology described previously eliminates the need for preemergence herbicide and minimizes the application of postemergence herbicide because only weeds are sprayed and significant amounts of bare soil is not sprayed. Considerable cost savings can result.

Figure 9A:
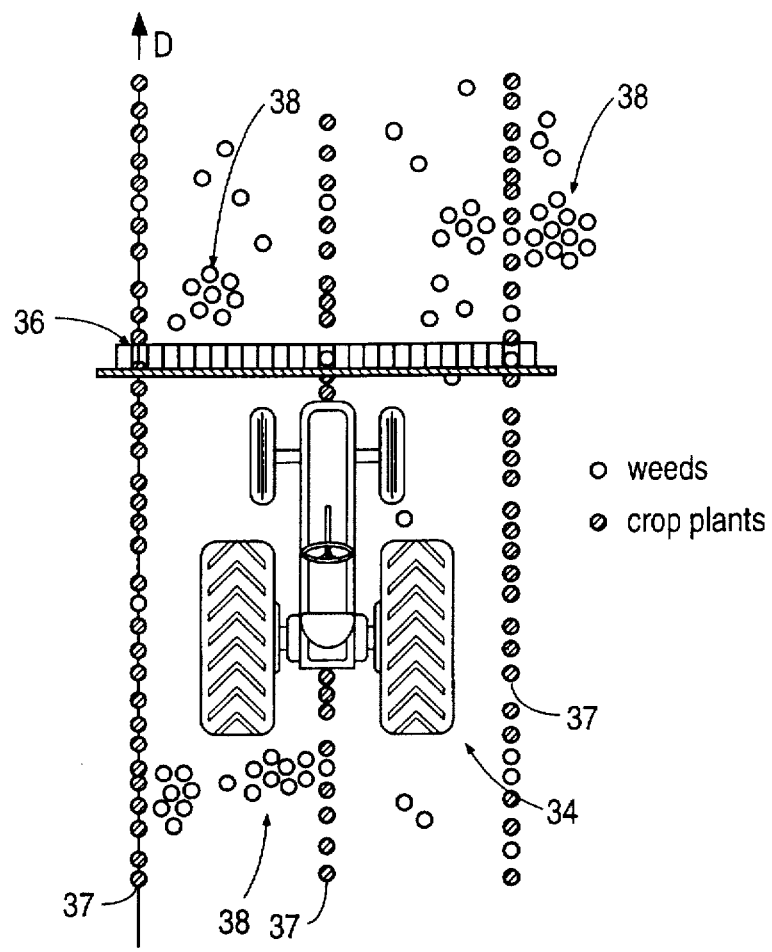
FIGS. 9A and 9B are diagrams illustrating a determination of the locations of rows of crop plants.
Figure 9B:
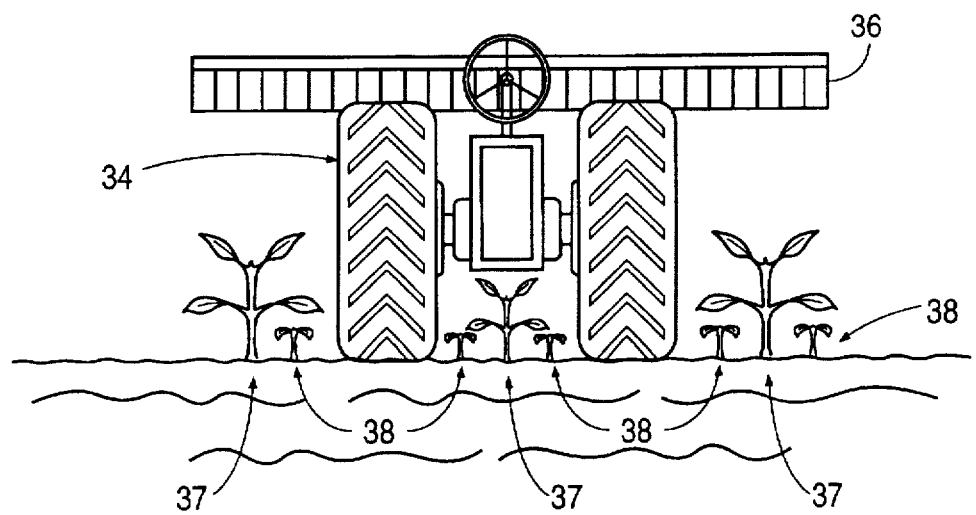

FIGS. 9A and 9B show a means for moving 34 (in this case a tractor) outfitted with a plurality of sensors 36 and a plurality of solenoid-operated spray nozzles (not shown). The sensors are mounted on a boom such that a strip of the field perpendicular to direction of tractor movement D is illuminated with modulated light. Distance information and information on whether an illuminated object has spectral reflectance indicative of crop plant, weed plant or soil is sent to a central digital processor (not shown). By storing past information on which sensors detect the most objects having special characteristics of plants and which sensors detect the most objects having heights consistent with the expected crop height, the central digital processor determines which illuminated objects having special plant characteristics are crop plants in rows 37 and which are randomly scattered weeds 38. Accordingly, the central digital processor disables the spray nozzles located over the rows 37 of crops. As a result, only the weeds 38 in the middles are sprayed. The row crops 38 are not sprayed and herbicide is not wasted on the bare ground in the middles.

Method #4

Row Crop Row Selective Crop Sprayer

In accordance with another embodiment, rows of crops are located as described above. Rather than spraying the middles with herbicide, however, the crop plant in the rows are sprayed with foliar nutrients, pesticide, selective herbicide or water.

Method #5

Vehicle or Implement Guidance

In many farming operations, a vehicle and/or implement is guided through rows of crops in a field. In cultivating row crops, for example, the cultivator implement is guided as fast as possible through the rows of crops so that the cultivator tines come as close as possible to the crops plants without damaging the crop itself. Manually guiding the vehicle and/or implement with respect to the rows is a demanding and tedious task. If, for example, the cultivator strays too close to a row, a section of the row of crop plants may be uprooted. Various automatic implement and vehicle guidance systems therefore have been developed to guide vehicles and implements with respect to rows of crops. None of these automatic vehicle guidance systems has, however, enjoyed broad market acceptance.

A furrow is formed between adjacent rows at the time the row crop is planted. "Mole balls" are physical weights which are dragged in such a furrow. As the vehicle moves through the field, the weight of mole ball keeps the mole ball in the furrow between rows. If the vehicle or implement strays toward either row, switches or valves are actuated which operate a hydraulic cylinder to adjust the direction of travel of the vehicle or implement.

Another vehicle guidance technique involves the use of wires or similar mechanical devices which make actual physical contact with the row crop plants. The mechanical touching devices are connected to switches which in turn control a hydraulic or other means of redirecting the vehicle or implement.

Still other vehicle guidance techniques use ultrasonic sonar and/or infrared detectors. An infrared method disclosed in U.S. Pat. No. 5,279,068 directs infrared radiation toward plants in two adjacent crop rows. The two magnitudes of the reflected infrared radiation are compared and the vehicle or implement is steered to keep the magnitudes of the two signals balanced thereby keeping the vehicle or implement centered between the two rows. This technique is believed to have problems due to weeds in the middle reflecting and giving incorrect data and due to voids in the row of crop plants not reflecting and not providing sufficient data. Accordingly, the above-described techniques exhibit problems when faced with situations involving fields without well contoured furrows, crop plants which are damaged by physical contact with the guidance device, and voids in crop rows where plants have not survived.

These problems are overcome in accordance with certain of the described embodiments. As set forth above in connection with FIGS. 9A and 9B, sensors 36 are mounted on the vehicle or implement. The sensors may be disposed to illuminate and therefore follow only one row. Alternatively, the sensors may illuminate and follow multiple rows as is illustrated in FIGS. 9A and 9B. Each sensor may output three types of information: 1) information indicative of whether there is an object at a suitable range from the sensor in the field of view, 2) information indicating whether an object in range in the field of view has spectral reflectance properties indicative of a plant crop, a weed, or another object, 3) and information indicative of a distance to the object. In some embodiments, the magnitude of total reflected radiation detected is the information indicating that an object is at a suitable range from the sensor in the field of view. A digital processor coupled to the sensor examines the output of each sensor periodically and stores the information in memory. The digital processor, with the aid of software composed for this purpose, compares the current data being gathered from the sensors to the data stored in memory. From the information available, the digital processor makes very accurate predictions on row location based on object sizes, object heights, ground topology and/or plant locations and spectral reflectance properties. Because the crop plants were planted at the same time in an accurate row pattern, they are probably of a somewhat consistent size. The processor is therefore able to determine accurately which plants are crop and which plants are weeds. Knowing which plants are the crop allows the processor to plot a line which represents the centerline of the crop row 37. In some embodiments, this information is put into a format which is accepted by currently available vehicle guidance systems.

In some embodiments, an implement is guided (for example, a cultivator) with respect to rows in a field.

Figure 9C:
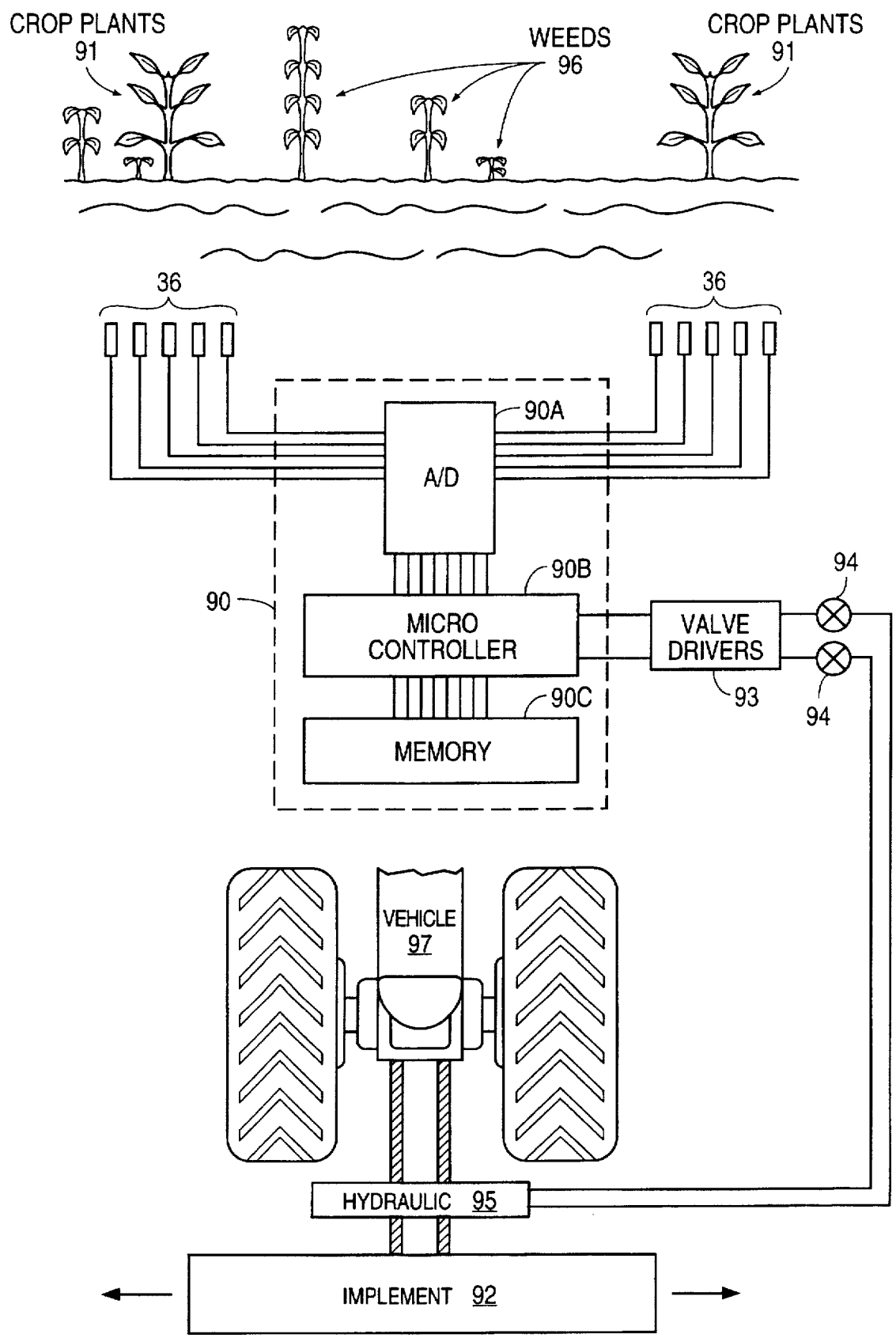
FIG. 9C is a diagram illustrating guidance of an implement such as a cultivator through a field of row crop plants using a hydraulic actuator.

FIG. 9C is a diagram illustrating a plurality of sensors 36 coupled to a digital processor 90. Digital processor 90 comprises a multi-input analog-to-digital converter 90A, microcontroller 90B and memory 90C. Digital processor 90 determines the locations of the rows of crop plants 91 and moves the implement 92 to the left or the right via valve drivers 93, valves 94 and hydraulic actuator 95. If, for example, the implement 92 is a cultivator, the digital processor 90 controls the location of the tines of the cultivator to uproot weeds 96 but to leave crop plants 91. Vehicle 97 may or may not be guided by the digital processor 90 through the rows of crops in the field. Voids in crop rows where plants have not survived does not cause the guidance system to fail.

In other embodiments, a vehicle guidance system does not use spectral information but rather uses only distance to object information. For example, where dead plants are to be harvested or where a vehicle or implement is to be guided through a recently planted field in which the seeds have not yet germinated, the distance information may be used to map soil contours and to locate furrows and rows accordingly.

Method #6

Mapping Objects in a Field

Some parts of a field may have different types of soil, may receive different amounts of runoff, may receive different amounts of direct sunlight, may have different types of pests, and may be subject to other environmental factors which affect plant growth in different ways. If information bearing on these different environmental factors could be easily gathered, such information could be used in determining how and when to till, to fertilize, and to harvest. It could be determined, for example, that certain parts of a field should be planted with one type of crop whereas other parts of the field should be planted with another type of crop.

In accordance with one embodiment, information to make a map of a field is gathered automatically when the field is traversed for another purpose such as cultivating. Information indicative of whether a strip of a field illuminated with modulated light contains soil, living crop plants, weeds or other objects, and the size of these plants or other objects is supplied by a sensor to a data storage device. The same sensor unit is able to determine the amount of organic material in the soil. As a tractor, picker, combine or other means for moving sweeps the sensor and data storage device across the field, the data storage device records the soil/plant information and distance information on a storage medium. A hard disk drive may be used. In some embodiments, the data storage device also receives position information from a global positioning system (GPS) device so that the detected characteristics of the field are mapped to the corresponding geographical locations in the field. In this way, characteristics of the field can be gathered, downloaded from the data storage device, and later analyzed. In fact, the analysis can be done in real time and application rates adjusted simultaneously. Using this technique, multiple field maps gathered during multiple growing seasons and for different types of crops can be compared and analyzed.

Method #7

Cotton In-Row Weed Sprayer

Many row crops are grown in rows with plants in each row spaced only a few inches apart. Rows may be spaced 30 to 40 inches apart. Typically plant spacing within each row is uneven so that the canopy of adjacent plants often grow into each other or conversely there could be gaps where no plants exist. In such a situation, it is possible to identify the centerline of the planted row (as discussed above) but it may not be possible to rely upon the plant spacing within the row for purposes of eliminating weeds growing between crop plants in the row. It is therefore desirable to discriminate between weeds and crop plants using more than plant/soil location information.

Cotton is a crop where it is desirable to discriminate between crop plants in rows and weeds between the crop plants in order to selectively eliminate weeds without damaging the crop plants. When the cotton plant is less than a few weeks old, its stalk is soft green tissue which is somewhat translucent to near infrared light. The stalk reflects strongly in the infrared portion of the spectrum and it appears to have much the same spectral reflectance as a weed might. It is therefore difficult to discriminate the cotton crop from the weed plants. At this stage of the crop development, one weeding method is to spray the rows with a continuous band of selective chemical herbicide which can be tolerated by the cotton crop (e.g., MSMA). Another method measures the differences in spectral reflectance, at certain wavelengths, of cotton plants versus that of the weed plants. Certain weed types can be discriminated from cotton plants on the basis of a different spectral reflectance and treated accordingly.

Figure 10:
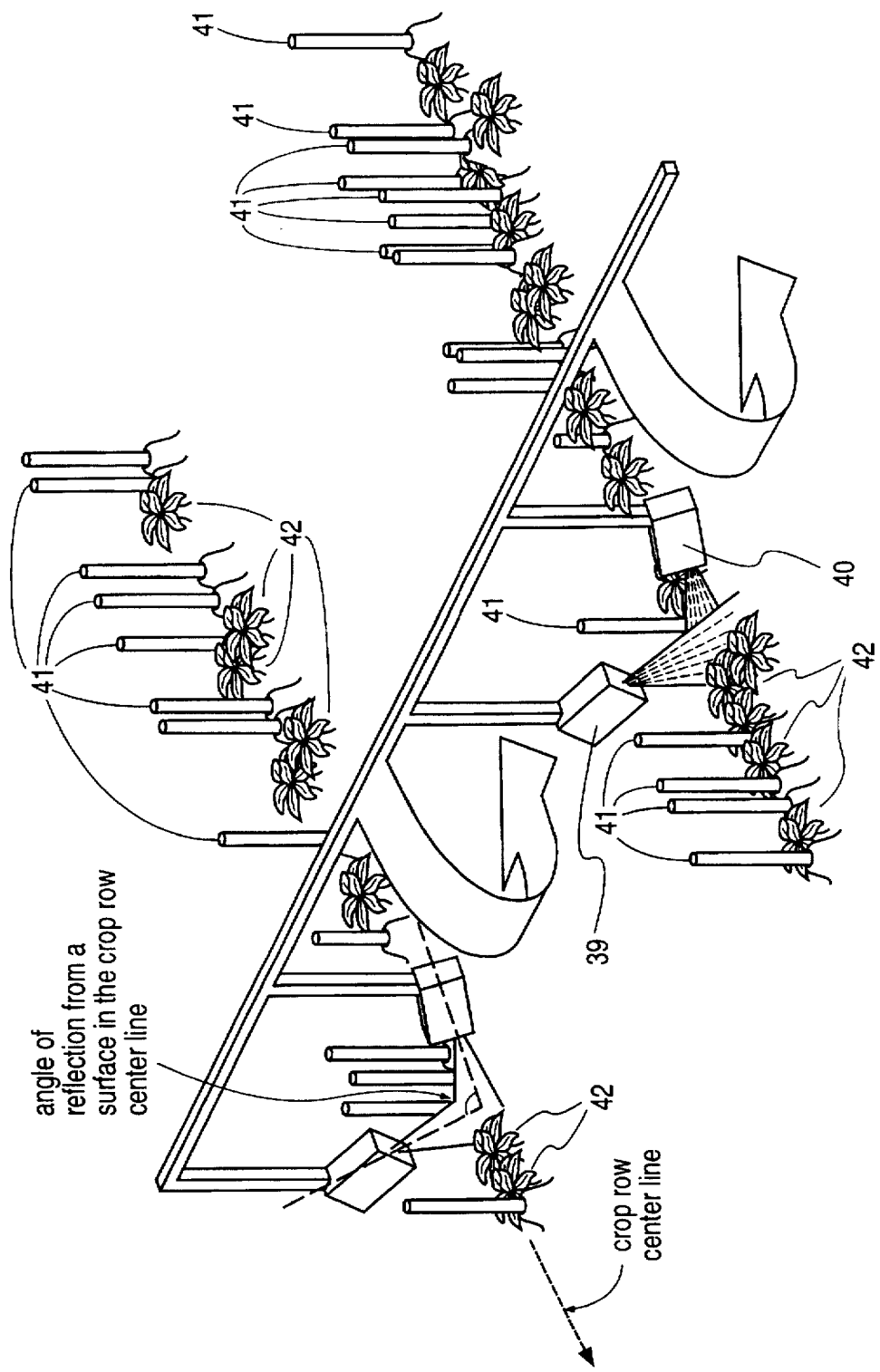
FIG. 10 is a diagram illustrating how weeds growing in the rows of cotton plants are detected and sprayed without spraying the cotton plants.

At a later stage, the cotton stalks become opaque but generally still have the spectral characteristics of weeds. At this point it is possible to discriminate cotton stalks in the rows from weeds in the rows. FIG. 10 shows a first sensor 39 located on one side of a row of cotton stalks 41 and second sensor 40 located on the other side of the row. In this embodiment, sensor 40 is oriented to receive only light modulated by sensor 39 and sensor 39 is oriented to receive only light modulated by sensor 40. Light reflecting off an object surface in the crop row centerline has an angle of reflection in excess of 45 degrees. In the specific embodiment illustrated, the angle of reflection exceeds 90 degrees.

Because the vertical cotton stalks 41 typically do not provide a reflecting surface that reflects light from one side of the row to the other, and because the weeds 41 having a different reflective surface profile do provide such a reflecting surface, the sensor does not detect modulated light reflected from cotton stalks but does detect modulated light reflected from weeds 42 in the cotton rows. The weeds 42 can therefore be selectively eliminated without damaging the cotton stalks 41.

At a later stage, the cotton stalks become woody and cease to be similar in spectral reflectance to weeds. The cotton crops can therefore be discriminated from the weeds using the normal spectral reflectance technique described earlier. Weeds in cotton can be eliminated using electronically-controlled plant-eliminating devices including automatic hoes and electronically-controlled herbicide applying spray nozzles.

Figure 11A:
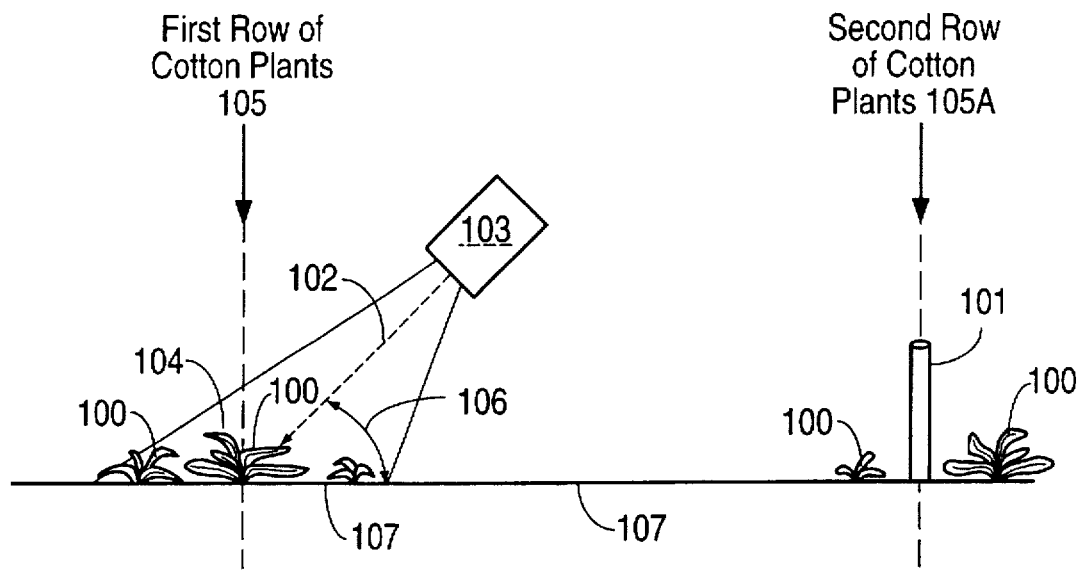
FIGS. 11A and 11B illustrate a method and apparatus for spraying herbicide onto weeds in a cotton field without spraying the stalks of the growing cotton plants.
Figure 11B:
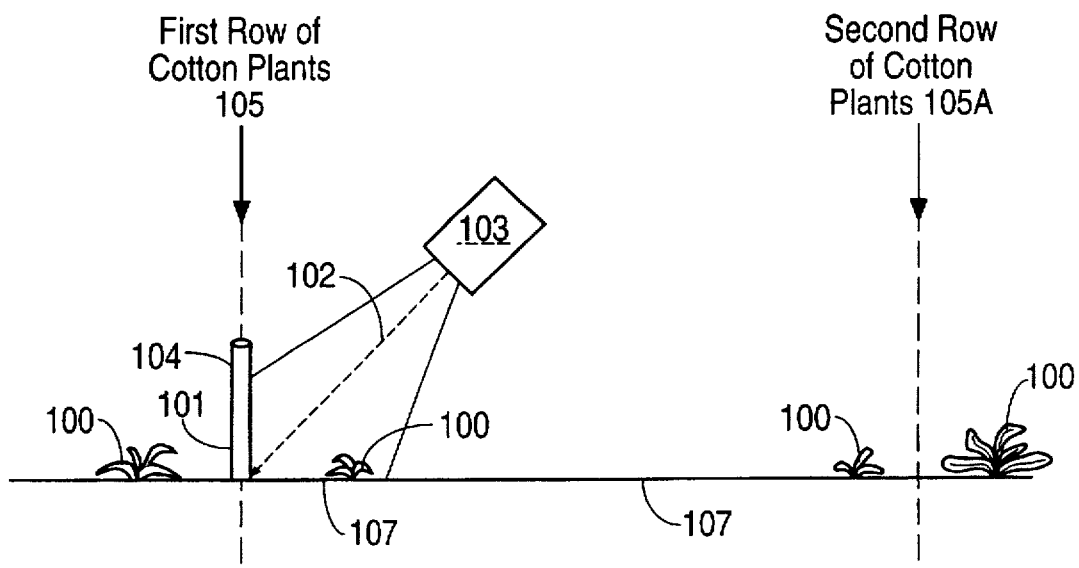

FIGS. 11A and 11B are diagrams illustrating a method and apparatus whereby weeds 100 which are growing around the bases of cotton stalks 101 are sprayed with herbicide without spraying substantial amounts of herbicide onto the cotton plants themselves. In FIGS. 11A and 11B, the majority of the leaves (not shown) of the cotton plants are disposed above the upper extent of the cotton stalk illustrations. Rather than transmitting light from one unit disposed on one side of a row of cotton plants and detecting reflected light in another unit disposed on the other side of the row (see FIG. 10), plant detecting techniques such as those disclosed in U.S. Pat. No. 5,296,702 are employed to transmit light 102 from a unit 103 toward an object 104 in or adjacent a row of cotton plants 105 and to receive in unit 103 a portion of that light which reflects off the object. The object can, for example, be a growing weed, a cotton stalk of a growing cotton plant, or bare ground. Light 102 is transmitted and received on the same side of the row 105 between row 105 and an adjacent row, row 105A. Distance determining techniques set forth in U.S. patent application Ser. No. 08/276,002 (the subject matter of which is incorporated herein by reference) may also be employed. In some embodiments, light 102 travels toward object 104 in row 105 at an angle 106 in the range of 30 to 60 degrees with respect to a surface 107 of the field.

The cotton plants in the rows are adequately mature that their stalks are woody and have a spectral characteristic which differs significantly from a spectral characteristic of a typical weed which would be growing in a cotton field. In one example, the growing weeds are Purple Nutsedge plants. In one example, the cotton plants are the Pima or Acala varieties of cotton, are at least six weeks old, and are at least eight inches tall. MSMA herbicide is used.

If unit 103 detects the reflected light and determines that the object 104 has the spectral characteristic of a growing weed (see FIG. 11A), then unit 103 causes herbicide to be sprayed onto the object 104. Any suitable technique for spraying herbicide onto a plant in a field can be used. If, on the other hand, unit 103 detects the reflected light and determines that the object 104 has another spectral characteristic (see FIG. 11B), then unit 103 does not cause herbicide to be sprayed onto object 104. Spectral characteristics other than the spectral characteristic of the growing weed include the spectral characteristic of woody cotton stalks and the spectral characteristic of soil. Because the majority of the leaves of the cotton plants is disposed above the area illuminated by the light 102 and is outside the area which can be sprayed, the majority of the leaves of the cotton plants is not sprayed with herbicide.

As illustrated, both weeds located in the line of the row and weeds located somewhat outside the line of the row are illuminated with light 102 and sprayed. Unit 103 may comprise one light emitting diode, photodetector and spray nozzle set or may comprise a plurality of such sets arranged in a row. If a single light emitting diode, photodetector and spray nozzle set is used, then the spectral information obtained will be the average of the spectral characteristics of all objects in the field of view of the set.

The unit may be moved through the cotton field parallel to the row 105 of cotton plants on an implement attached to and/or drawn by a tractor or other suitable vehicle. In some embodiments there is one unit for each row, whereas in other embodiments there are two units for each row, one disposed on each side of the row. In some embodiments unit 103 uses an electronically-controlled valve (part number 9X37 manufactured by KIP Incorporated) to control the application of herbicide. A magnetized metal filter may be employed to remove particles from the herbicide which might otherwise plug the valve.

Method #8

Detecting Dissimilar Objects in a Flow of Grain

Harvesting equipment is particularly prone to being damaged by picking up rocks and other hard objects. A sensor (as described above) is used to detect the presence of rocks or metal fragments in the flow of crop material in harvesting equipment and to disengage power before damage can result. The field-of-view of a sensor capable of determining a spectral reflectance of an object is aligned across the flow of the crop material in the harvesting equipment. The background may be a pipe, wall or panel having a particular spectral reflectance, the flow of crop material flowing between the sensor and the background. Crop material flowing through the field of view of the sensor results in a certain spectral signature being detected by the sensor. In the event that the crop has a spectral characteristic of a living plant 30 such as is shown in FIG. 6, introduction of a rock into the flow of crop material will result in a substantially different spectral characteristic being detected. The difference in spectral characteristics is used to detect the rock and to disengage power from the harvesting equipment.

Method #9

Detecting a Parasitic Weed in a Field of Crop Plants

A parasitic weed is discriminated from a crop plant. Line 30A in FIG. 6 shows the spectral reflectance of a parasitic weed known as Dodder versus wavelength. Dodder germinates from a seed which may lie dormant in the ground for up to ten years. When about 2 to 3 inches tall, the Dodder plant finds a host (the host could be a safflower plant, a tomato plant, or an alfalfa plant). The young Dodder plant attaches itself to the host, grows up into the host plant, severs its own roots to the soil, and lives parasitically from its host. When mature, the Dodder plant looks much like a ball of orange colored spaghetti. Being orange, it has a different spectral reflectance characteristic in the visible spectrum which differentiates it from a chlorophyll bearing host plant. Because Dodder has very little chlorophyll, the spectral reflectance curve for Dodder does not have as large of a chlorophyll absorption dip at 670 nanometers as do host plants having larger amount of chlorophyll.

In accordance with one embodiment, spectral reflectance at two wavelengths is measured. As illustrated in FIG. 6, an ordinary crop plant typically has a larger difference between the reflectance at wavelengths 670 nanometers and the reflectance at 770 nanometers than the parasitic Dodder weed. The magnitude of the difference in spectral reflectance at these two characteristic wavelengths is used to discriminate light reflecting from the parasitic weed from light reflecting from the crop plant. After the parasitic weed is identified in the field and distinguished from the crop plants, the parasitic weed is automatically eliminated by selective spraying or selective cultivation. Over a period of years, all parasitic weeds and seeds of parasitic weeds are eliminated from the field.

Although the present invention has been described by way of the presently described specific embodiments, the invention is not limited thereto. Adaptations, modifications and various combinations of different aspects of the specific embodiments may be practiced without departing from the spirit and scope of the invention. The term "light" is not limited to visible light, but rather includes infrared radiation, ultraviolet radiation, and electromagnetic radiation of other suitable frequencies. The above description is presented merely for illustrative instructional purposes and is not intended to limit the scope of the invention as set forth in the following claims.

We claim:

1. A method, comprising:
   (a) transmitting light onto a first object in a field, said first object being a living plant other than a cotton plant;
   (b) detecting a portion of said light which reflects off said first object and obtaining spectral information indicative of said first object;
   (c) transmitting light onto a second object in said field, said second object being a stalk of a living cotton plant;
   (d) detecting a portion of said light which reflects off said second object and obtaining spectral information indicative of said second object;
   (e) differentiating said first object from said second object using said spectral information indicative of said first object and said spectral information indicative of said second object; and
   (f) using an electronically-controlled valve to apply herbicide onto said first object and to apply substantially no herbicide onto said second object.

2. The method of claim 1, further comprising:
   (g) moving a source of said light and said electronically-controlled valve together through said field, said source of light generating said light of step (a) and said light of step (c).

3. The method of claim 1, wherein a first row of cotton plants and a second row of cotton plants are disposed in said field, said light being transmitted in step (c) from a location between said rows.

4. A method, comprising:
   (a) transmitting light onto a first object in a field, said first object being a living plant other than a cotton plant;
   (b) detecting a portion of said light which reflects off said first object and obtaining spectral information indicative of said first object;
   (c) transmitting light onto a second object in said field, said second object being a stalk of a living cotton plant;
   (d) detecting a portion of said light which reflects off said second object and obtaining spectral information indicative of said second object;
   (e) differentiating said first object from said second object using said spectral information indicative of said first object and said spectral information indicative of said second object; and
   (f) using an electronically-controlled valve to apply herbicide onto said first object and to apply substantially no herbicide onto said second object, wherein at least six weeks have passed between the time said cotton plant germinated and the time step (f) is performed.

5. A method, comprising:
   (a) transmitting light onto a first object in a field, said first object being a living plant other than a cotton plant;
   (b) detecting a portion of said light which reflects off said first object and obtaining spectral information indicative of said first object;

(c) transmitting light onto a second object in said field, said second object being a stalk of a living cotton plant;

(d) detecting a portion of said light which reflects off said second object and obtaining spectral information indicative of said second object;

(e) differentiating said first object from said second object using said spectral information indicative of said first object and said spectral information indicative of said second object; and (f) using an electronically-controlled valve to apply herbicide onto said first object and to apply substantially no herbicide onto said second object, wherein said cotton plant is at least eight inches tall.

6. A method, comprising:

(a) transmitting light onto a first object in a field, said first object being a living plant other than a cotton plant;

(b) detecting a portion of said light which reflects off said first object and obtaining spectral information indicative of said first object;

(c) transmitting light onto a second object in said field, said second object being a stalk of a living cotton plant;

(d) detecting a portion of said light which reflects off said second object and obtaining spectral information indicative of said second object;

(e) differentiating said first object from said second object using said spectral information indicative of said first object and said spectral information indicative of said second object; and (f) using an electronically-controlled valve to apply herbicide onto said first object and to apply substantially no herbicide onto said second object, wherein said field has a surface, and wherein said light is transmitted in step (c) such that said light travels toward said second object at an angle in the range of 30 to 60 degrees with respect to said surface.

7. The method of claim 1, further comprising:

(g) transmitting light onto a third object in said field, said third object being soil;

(h) detecting a portion of said light which reflects off said third object and obtaining spectral characteristic information indicative of said third object;

(i) differentiating said third object from said first object using said spectral characteristic information indicative of said third object; and (j) using said electronically-controlled valve to apply substantially no herbicide onto said third object.

8. A method, comprising:

detecting light reflecting off a cotton stalk in a field and obtaining first spectral information therefrom;

detecting light reflecting off a growing plant in said field other than a cotton plant and obtaining second spectral information therefrom;

distinguishing said cotton stalk from said growing plant using said first and second spectral information;

using an electronically-controlled valve to apply herbicide onto said growing plant and to apply substantially no herbicide onto said cotton stalk.

9. The method of claim 8, further comprising:

moving a source of said light and said electronically-controlled valve together through said field, said source of light generating said light reflecting off said cotton stalk and said light reflecting off said growing plant.

10. Structure, comprising:

means for distinguishing a cotton stalk of a growing cotton plant in a field from another growing plant in said field, said another growing plant being a plant other than a cotton plant; and means for applying herbicide onto said another growing plant without applying a substantial amount of herbicide onto said cotton stalk.

11. The structure of claim 10, wherein said another growing plant is growing between adjacent cotton plants in a row of cotton plants.

12. The structure of claim 10, further comprising:

means for moving said means for distinguishing and said means for applying together through said field.

13. The structure of claim 10, wherein said means for distinguishing comprises:

means for transmitting substantially monochromatic light of a first wavelength;

means for transmitting substantially monochromatic light of a second wavelength; and means for detecting light.

14. The structure of claim 10, wherein said means for distinguishing transmits light from a first side of a row of cotton plants and detects a portion of said light from the same side of said row, said cotton stalk being a part of a cotton plant growing in said row.

* * * * *